United States Patent
Dillon et al.

(10) Patent No.: US 12,011,316 B2
(45) Date of Patent: Jun. 18, 2024

(54) BLOOD FLOW MONITORS AND METHODS OF MONITORING CHARACTERISTICS OF TISSUE

(71) Applicant: CooperSurgical, Inc., Trumbull, CT (US)

(72) Inventors: Travis Dillon, Winston-Salem, NC (US); Suresh Dwarakaprasad, Medford, NJ (US); David Edwin Petroskey, Lorain, OH (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 17/967,926

(22) Filed: Oct. 18, 2022

(65) Prior Publication Data

US 2023/0127280 A1  Apr. 27, 2023

Related U.S. Application Data

(60) Provisional application No. 63/271,453, filed on Oct. 25, 2021.

(51) Int. Cl.
| | | |
|---|---|---|
| *A61B 8/00* | (2006.01) | |
| *A61B 8/06* | (2006.01) | |
| *A61B 8/08* | (2006.01) | |

(52) U.S. Cl.
CPC .............. *A61B 8/06* (2013.01); *A61B 8/463* (2013.01); *A61B 8/488* (2013.01)

(58) Field of Classification Search
CPC ............ A61B 8/06; A61B 8/463; A61B 8/488
See application file for complete search history.

(56) References Cited

U.S. PATENT DOCUMENTS

| | | |
|---|---|---|
| 4,501,279 A | 2/1985 | Seo |
| 5,052,395 A | 10/1991 | Burton et al. |
| 6,616,611 B1 | 9/2003 | Moehring |
| 6,682,483 B1 | 1/2004 | Abend et al. |
| 7,796,247 B2 | 9/2010 | Mao et al. |

(Continued)

OTHER PUBLICATIONS

Doppler Blood Flow Monitoring System, Monitoring you can trust., Illustration by Lisa Clark, 2021, OHNS-D60784-EN-F, retrieved from Internet, Nov. 11, 2022, URL: https://www.cookmedical.com/data/resources/OHNS-D60784-EN-F_M3_1625833223863.pdf.

(Continued)

*Primary Examiner* — Joel F Brutus
(74) *Attorney, Agent, or Firm* — Fish & Richardson P.C.

(57) ABSTRACT

Blood flow monitors and methods of monitoring characteristics of tissue are described. An example method of monitoring characteristics of tissue includes: placing a tissue flap at a point of treatment, the tissue flap is a section of tissue that includes a blood vessel; attaching a first sensor to the tissue flap to monitor blood flow through the blood vessel; attaching the first sensor to a blood flow monitor that has a first visual display field and a second visual display field; attaching a second sensor to the tissue flap to monitor a characteristic of the tissue flap; attaching the second sensor to the blood flow monitor; activating the blood flow monitor to observe the blood flow through the first blood vessel and the characteristic of the tissue flap; and monitoring the blood flow through the first blood vessel over a period of time and the characteristic of the tissue flap.

20 Claims, 7 Drawing Sheets

(56) References Cited

U.S. PATENT DOCUMENTS

| | | | |
|---|---|---|---|
| 9,028,415 B2 | 5/2015 | Henry | |
| 9,820,718 B2 | 11/2017 | Flomerfelt et al. | |
| 10,732,269 B2 | 8/2020 | Hope Simpson et al. | |
| 10,751,025 B2 | 8/2020 | Rajagopal et al. | |
| 2006/0149154 A1 | 7/2006 | Stephens et al. | |
| 2013/0116575 A1 | 5/2013 | Mickle et al. | |
| 2014/0316215 A1* | 10/2014 | Shuler | A61B 5/742 |
| | | | 600/301 |
| 2015/0281853 A1 | 10/2015 | Eisner et al. | |
| 2017/0296139 A1* | 10/2017 | Giaya | A61B 5/0261 |
| 2019/0320984 A1 | 10/2019 | Elliott et al. | |

OTHER PUBLICATIONS

Doppler Blood Flow Monitor, Product Page, Retrieved from Internet Nov. 1, 2022, URL: https://www.cookmedical.com/products/33eecd89-149b-4d3c-955a-213541b21142/.

* cited by examiner

BLOOD FLOW MONITORS AND METHODS OF MONITORING CHARACTERISTICS OF TISSUE

RELATED APPLICATIONS

This application claims the benefit of U.S. Provisional Application No. 63/271,453, which was filed on Oct. 25, 2021. The entire disclosure of this related application is hereby incorporated by reference into this disclosure.

FIELD

The disclosure relates generally to the field of medical devices and associated methods. More particularly, the disclosure relates to blood flow monitors and methods of monitoring characteristics of tissue.

BACKGROUND

Blood flow monitoring is performed during a variety of procedures. For example, blood flow monitoring is commonly performed to confirm blood flow through a blood vessel in an implanted tissue flap and to confirm the overall health of the tissue flap. Conventionally, this monitoring depends upon direct listening to audible representations of the blood flow through speakers included in a blood flow monitor. As a result, effective and timely blood flow monitoring using currently available monitors necessitates the physical presence of the clinician in the patient room each time monitoring is desired or recommended, preventing the clinician from performing other tasks and/or visiting other patients. This can impede overall efficiency in the delivery of care since tissue flap implantation generally requires multiple rounds of monitoring, particularly during the initial hours following flap implantation.

Current blood flow monitors have other drawbacks, too. For example, current blood flow monitors fail to provide any representation, graphical or otherwise, of blood flow data over time, providing instead a single visual data point relating to the blood flow through a blood vessel (e.g., velocity at a point in time). This visual data point is generally represented as a single bar graph on the monitor (e.g., light emitting diode (LED) bar graph). Monitors that represent data in this manner fail to provide data trends, which could assist with reducing false positives that lead to unnecessary intervention and false negatives that lead to flap loss.

A need exists, therefore, for new and useful blood flow monitors and methods of monitoring characteristics of tissue.

SUMMARY OF SELECTED EXAMPLE EMBODIMENTS

Various example blood flow monitors and methods of monitoring characteristics of tissue are described herein.

An example method of monitoring characteristics of tissue includes: placing a tissue flap at a point of treatment, the tissue flap is a section of tissue that includes a first blood vessel; attaching a first sensor to the tissue flap to monitor blood flow through the first blood vessel, the first sensor attached to the first blood vessel such that it contacts the first blood vessel; attaching the first sensor to a blood flow monitor that has a first visual display field and a second visual display field; attaching a second sensor to the tissue flap to monitor a characteristic of the tissue flap, the second sensor is different than the first sensor; attaching the second sensor to the blood flow monitor; activating the blood flow monitor to observe the blood flow through the first blood vessel and the characteristic of the tissue flap, the first visual display field shows blood flow over time, the second visual display field shows the characteristic of the tissue flap; and monitoring the blood flow through the first blood vessel over a period of time and the characteristic of the tissue flap using the blood flow monitor.

An example blood flow monitor includes a first visual display field, a second visual display field, a third visual display field, a fourth visual display field, a first channel port, and a second channel port. The blood flow monitor is moveable between an off state and an on state. In the on state, the first visual display field shows data received from a first sensor that relates to blood flow over time for a first blood vessel of a tissue flap, the second visual display field shows data received from a second sensor that relates to a characteristic of the tissue flap, the third visual display field shows data that relates to the frequency domain of the blood flow over time, and the fourth visual display field shows data that relates to a combination of the blood flow over time and the frequency domain of the blood flow over time.

Additional understanding of these example blood flow monitors and methods of monitoring characteristics of tissue can be obtained by review of the detailed description, below, and the appended drawings.

DETAILED DESCRIPTION OF SELECTED EXAMPLES

The following detailed description and the appended drawings describe and illustrate various example embodiments of blood flow monitors and methods of monitoring characteristics of tissue. The description and illustration of these examples are provided to enable one skilled in the art to make and use a blood flow monitor and practice a method of monitoring characteristics of tissue. They are not intended to limit the scope of the claims in any manner. The invention is capable of being practiced or carried out in various ways and the examples described and illustrated herein are merely selected examples of the various ways of practicing or carrying out the invention and are not considered exhaustive.

Various methods of monitoring characteristics of tissue are described herein. While the methods described herein are shown and described as a series of acts, it is to be understood and appreciated that the methods are not limited by the order of acts, as some acts may in accordance with these methods occur in the order shown and/or described, in different orders, concurrently with other acts described herein, or be omitted.

Figure 1:
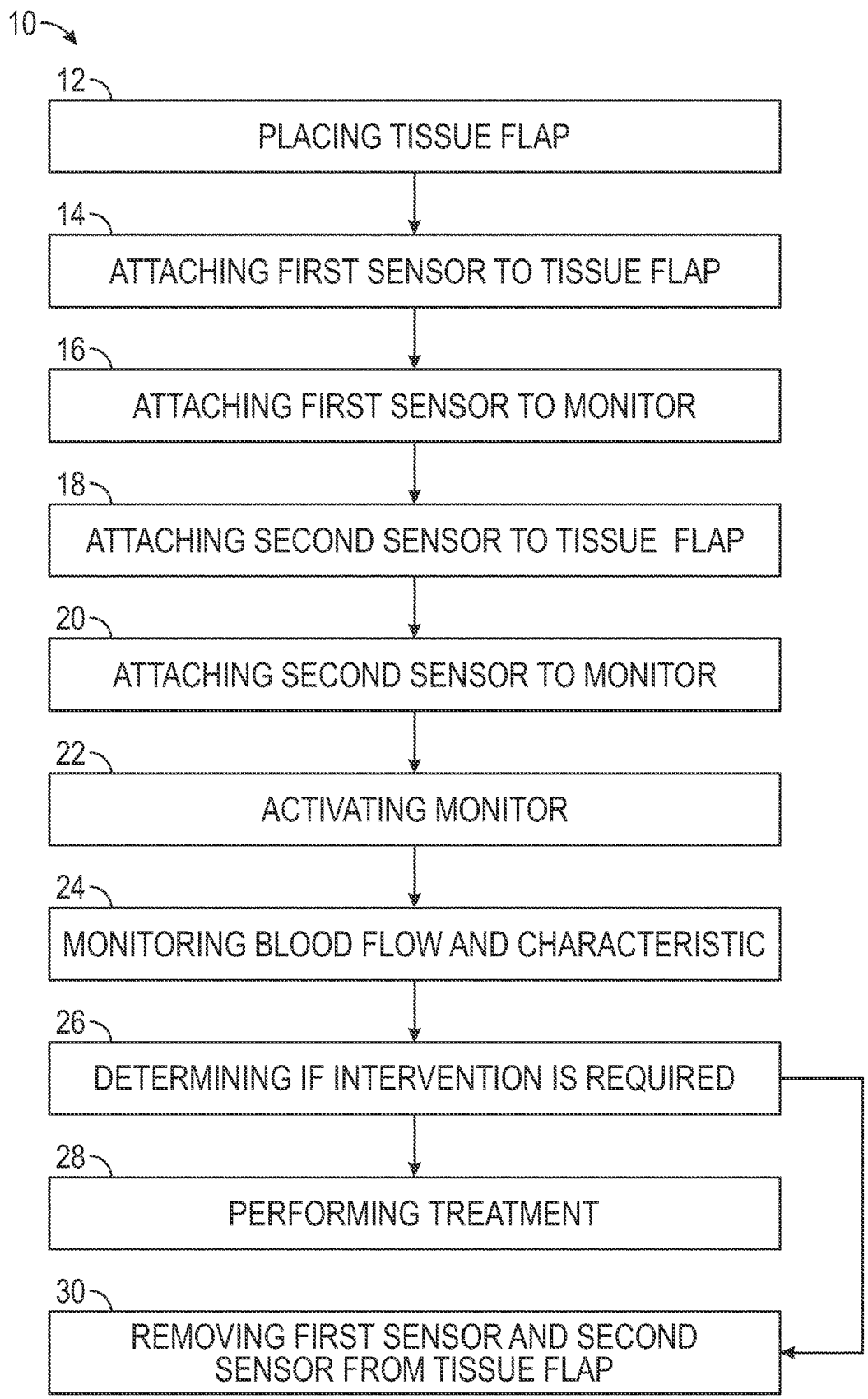
FIG. 1 is a schematic illustration of an example method of monitoring characteristics of tissue.

FIG. 1 is a schematic illustration of an example method 10 of monitoring characteristics of tissue.

A step 12 comprises placing a tissue flap at a point of treatment. The tissue flap includes a section of tissue that includes a first blood vessel. Another step 14 comprises attaching a first sensor to the tissue flap to monitor blood flow through the first blood vessel. The first sensor is attached to the tissue flap such that it contacts the first blood vessel. Another step 16 comprises attaching the first sensor to a blood flow monitor that has a first visual display field and a second visual display field. Another step 18 comprises attaching a second sensor to the tissue flap to monitor a characteristic of the tissue flap. The second sensor is different than the first sensor. Another step 20 comprises attaching the second sensor to the blood flow monitor. Another step 22 comprises activating the blood flow monitor to observe the blood flow through the first blood vessel and the characteristic of the tissue flap. Another step 24 comprises monitoring the blood flow through the first blood vessel over a period of time and the characteristic of the tissue flap. Another step 26 comprises determining if the blood flow through the first blood vessel and the characteristic of the tissue flap indicate intervention is required. If intervention is required, another step 28 comprises performing treatment. If intervention is not required, another step 30 comprises removing the first sensor from the tissue flap and removing the second sensor from the tissue flap.

Step 12 can be accomplished by placing the tissue flap at any suitable point of treatment and selection of a suitable point of treatment can be based on various considerations, such as the treatment intended to be performed. Examples of points of treatment considered suitable to place a tissue flap include the head (e.g., face), neck, chest, breast, back, abdomen, arms, buttocks, legs (e.g., thighs), areas of a body that previously included defects, such as those from an injury or other surgery (e.g., mastectomy), and any other point of treatment considered suitable for a particular embodiment.

A tissue flap utilized in a method of monitoring characteristics of tissue can comprise any suitable section of tissue that can be used to complete an autologous tissue reconstruction procedure, includes at least one blood vessel, and/or that has been moved from a donor site of a patient to a recipient site of the patient. Examples of tissue flaps considered suitable to complete a method of monitoring characteristics of tissue include local flaps (e.g., advancement flaps, rotation flaps, transposition flaps, interpolation flaps), free flaps, transverse rectus abdominis muscle flaps, deep inferior epigastric perforator flaps, latissimus dorsi flaps, gluteal artery perforator flaps, transverse upper gracilis flaps, flaps obtained from the chest, breast, back, abdomen, arms, buttocks, or legs (e.g., thighs) of a patient, combinations of those described herein, and any other tissue flap considered suitable for a particular embodiment.

Figure 2:
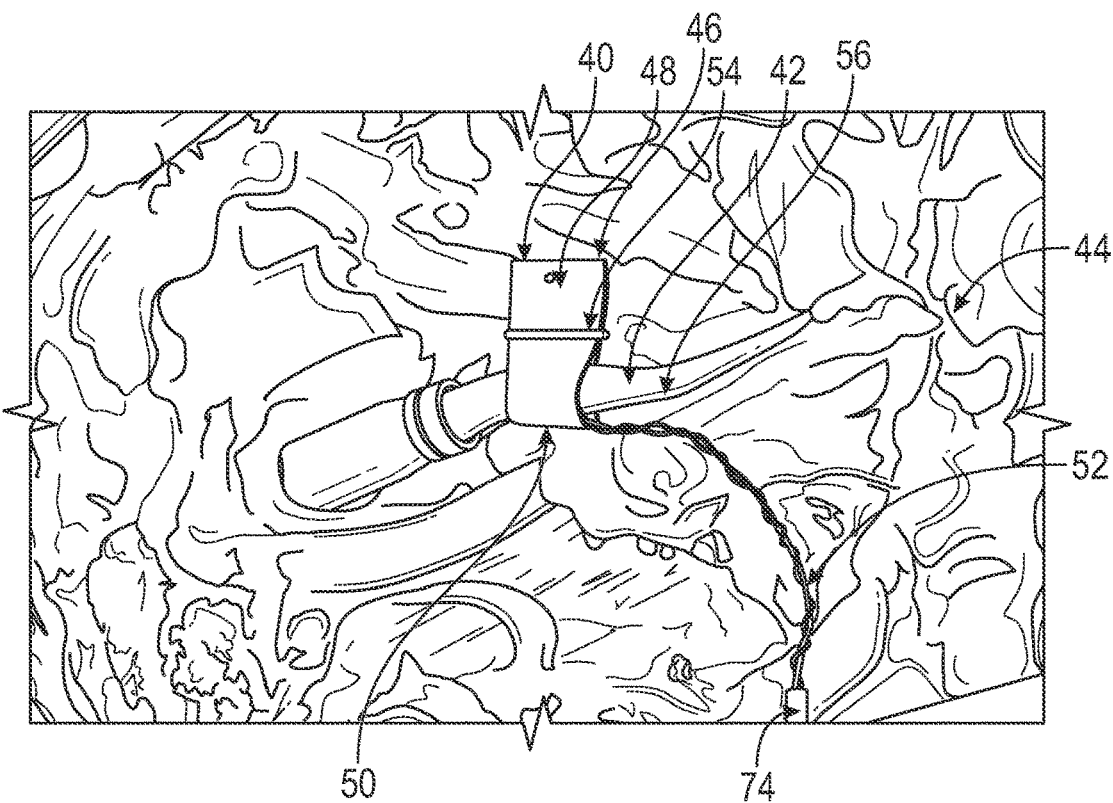
FIG. 2 is a partial perspective view of a first sensor attached to a tissue flap.

Step 14 can be accomplished by attaching any suitable first sensor to the tissue flap such that the first sensor contacts the first blood vessel. FIG. 2 illustrates a first sensor 40 contacting a first blood vessel 42 of a tissue flap 44 (e.g., directly contacting the first blood vessel 42). In the illustrated embodiment, the first sensor 40 is a Doppler probe 46 that includes a cuff 48, a probe crystal 50 attached to the cuff 48, and a wire member 52 attached to the probe crystal 50. The first sensor 40 is attached to the first blood vessel 42 by wrapping the cuff 48 around the first blood vessel 42 and attaching the cuff 48 directly to the first blood vessel 42 (e.g., surgically) using a surgical clip 54. The first sensor 40 allows for monitoring of blood flow within the first blood vessel 42 intraoperatively and postoperatively following completion of a procedure (e.g., reconstructive procedure). In the illustrated embodiment, the first sensor 40 is disposed deep within the tissue flap 44 (i.e., beneath a surface of the flap 44, subcutaneously) and is attached to the blood vessel 42, which in the illustrated embodiment is a vein 56. However, in alternative embodiments, a first sensor can be positioned at any suitable location on, or within, a tissue flap and can be attached to any suitable blood vessel, such as an artery.

While the first sensor 40 has been illustrated as a Doppler probe 46, a sensor used to complete a method of monitoring characteristics of tissue can include any suitable sensor capable of monitoring blood flow through a blood vessel and selection of a suitable sensor can be based on various considerations, such as the type of a tissue flap being used to complete the method. Examples of sensors considered suitable to use as a first sensor include in vivo sensors, ultrasonic probes, electromagnet probes, Doppler probes, such as Cook-Swartz Doppler probes, sensors that include components capable of transmitting and/or receiving data wirelessly, combinations of the sensors described herein, and any other sensor considered suitable for a particular embodiment. While the first sensor 40 has been illustrated as including various components and as being attached to the first blood vessel 42 in a particular manner, a sensor can include any suitable number of components and be attached to a blood vessel in any suitable manner. Selection of a suitable number of components for a sensor to include and of a suitable method or technique to attach a sensor to a blood vessel can be based on various considerations, including the material forming the sensor and/or the size and/or location of the blood vessel.

Figure 3:
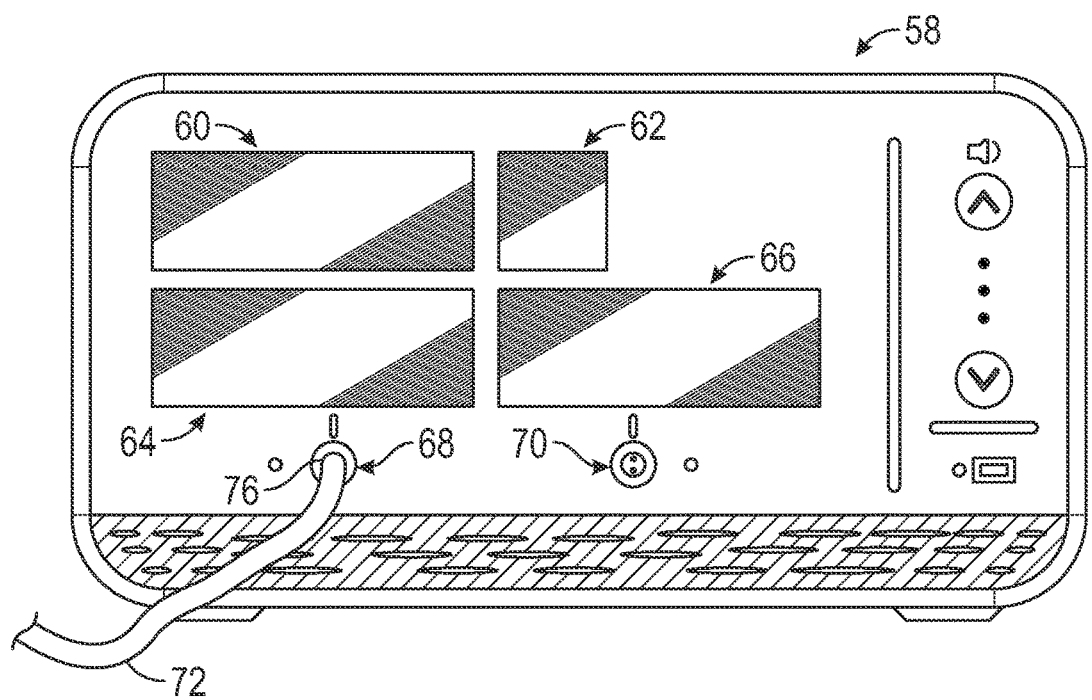
FIG. 3 is a partial elevation view of an example blood flow monitor. The first sensor is attached to the monitor using a first extension cable and the monitor is in the off state.

Step 16 can be accomplished by attaching the first sensor to any suitable blood flow monitor that has a first visual display field and a second visual display field. FIG. 3 illustrates an example blood flow monitor 58 considered suitable to attach the first sensor 40 illustrated in FIG. 2. The blood flow monitor 58 has a first visual display field 60, a second visual display field 62, a third visual display field 64, a fourth visual display field 66, a first channel port 68, and a second channel port 70. The blood flow monitor 58 is moveable between an off state and an on state. FIG. 3 illustrates the blood flow monitor 58 in the off state. In the illustrated embodiment, the first sensor 40 is attached to the blood flow monitor 58 using a first extension cable 72 that has a first end 74 attached to the first sensor 40 and a second end 76 attached to the blood flow monitor 58 (e.g., first channel port 68). However, in alternative embodiments, a first sensor can be attached directly to a blood flow monitor without using an extension cable.

While the blood flow monitor 58 has been illustrated as having a particular number of visual display fields (e.g., discrete portions of a display, discrete displays) and as having a particular number of channel ports, a blood flow monitor can include any suitable number of visual display fields, channel ports, and other components, features, and/or devices. Selection of a suitable number of visual display fields and/or channel ports to include in a blood flow monitor can be based on various considerations, including the number of sensors being utilized to monitor a tissue flap. Examples of numbers of visual display fields and/or channel ports considered suitable to include in a blood flow monitor include one, at least one, two, a plurality, three, four, five, more than five, and any other number considered suitable for a particular embodiment. Examples of other components, features, and/or devices considered suitable to include in a blood flow monitor include those described herein, one or more speakers, one or more amplifiers, and any other component considered suitable for a particular embodiment. Depending on the type of sensors being utilized, a blood flow monitor can also include one or more components capable of receiving and/or transmitting data wirelessly, such as receiving data wirelessly from one or more sensors and/or transmitting data wirelessly to a network such that data received by one or more sensors and/or data displayed within a visual display field can be provided to a remote device (e.g., remote storage device) and/or a user (e.g., physician) via a remote app (e.g., on a mobile device, on a tablet, on a cellular phone).

Figure 4:
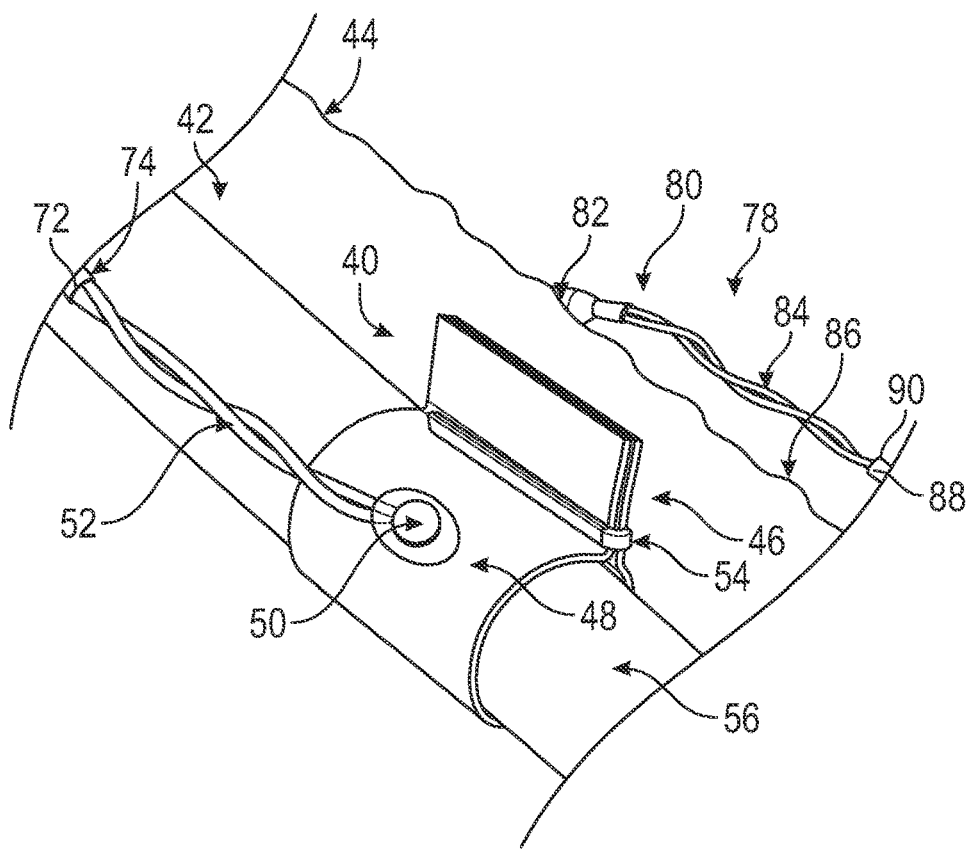
FIG. 4 is a partial perspective view of a second sensor attached to the tissue flap illustrated in FIG. 2.

Step 18 can be accomplished by attaching any suitable second sensor to the tissue flap such that the second sensor contacts the tissue flap. FIG. 4 illustrates the first sensor 40 contacting the first blood vessel 42 of the tissue flap 44 and a second sensor 78 contacting the tissue flap 44 (e.g., directly contacting the tissue flap 44). The second sensor 78 is different than the first sensor 40. In the illustrated embodiment, the second sensor 78 is a tissue oxygen saturation sensor (StO2 sensor) 80 that includes a surface sensor 82 and a wire member 84 attached to the surface sensor 82. Use of a StO2 sensor provides a mechanism for detecting compromises in tissue viability before obvious clinical signs and direct monitoring of the tissue (e.g., using a first sensor (e.g., Doppler probe and/or a second sensor) provides additional evidence of tissue viability. The second sensor 78 is attached to a surface 86 of the tissue flap 44 (e.g., superficially relative to the first sensor 40) by attaching the surface sensor 82 directly to the surface 86 of the tissue flap 44 (e.g., using adhesive). The second sensor 78 allows for monitoring of a characteristic of the tissue flap 44 that is different than the characteristic being monitored by the first sensor 40. In the illustrated embodiment, the second sensor 78 allows for monitoring of the tissue oxygenation saturation of the tissue flap 44 intraoperatively and postoperatively following completion of a procedure (e.g., reconstructive procedure).

While the second sensor 78 has been illustrated as a tissue oxygenation saturation sensor 80, a sensor used to complete a method of monitoring characteristics of tissue can include any suitable sensor capable of monitoring any suitable characteristic of a tissue flap. Selection of a suitable sensor can be based on various considerations, such as the type of a tissue flap being used to complete the method. Examples of sensors considered suitable to use as a second sensor include in vivo sensors, surface sensors, near-infrared light sensors (e.g., StO2 sensors), sensors that include components capable of transmitting and/or receiving data wirelessly, combinations of the sensors described herein, and any other sensor considered suitable for a particular embodiment. Examples of characteristics considered suitable for a second sensor to monitor include tissue oxygen saturation, temperature, blood pressure, orifice diameter (e.g., artificial, original), pulse, coagulation factors, and any other characteristic considered suitable for a particular embodiment. While the second sensor 78 has been illustrated as including various components and as being attached to the tissue flap 44 in a particular manner and at a particular location on the tissue flap 44 (e.g., adjacent the first sensor 40), a second sensor can include any suitable number of components, be attached to a tissue flap in any suitable manner, and be disposed at any suitable location on a tissue flap. Selection of a suitable number of components for a sensor to include, of a suitable method or technique to attach a sensor to a tissue flap, and/or of a suitable location to position a second sensor on a tissue flap can be based on various considerations, including the material forming the sensor and/or the size and/or location of the implant site of the tissue flap. Examples of locations considered suitable to position a second sensor include superficially, superficially relative to a first sensor, subcutaneously, adjacent to a first sensor, between a first sensor and an edge of a tissue flap, combinations of the locations described herein, and another location considered suitable for a particular embodiment. A second sensor can omit the inclusion of a surface sensor and include other sensor components depending on the location at which a second sensor is positioned on a tissue flap.

Figure 5:
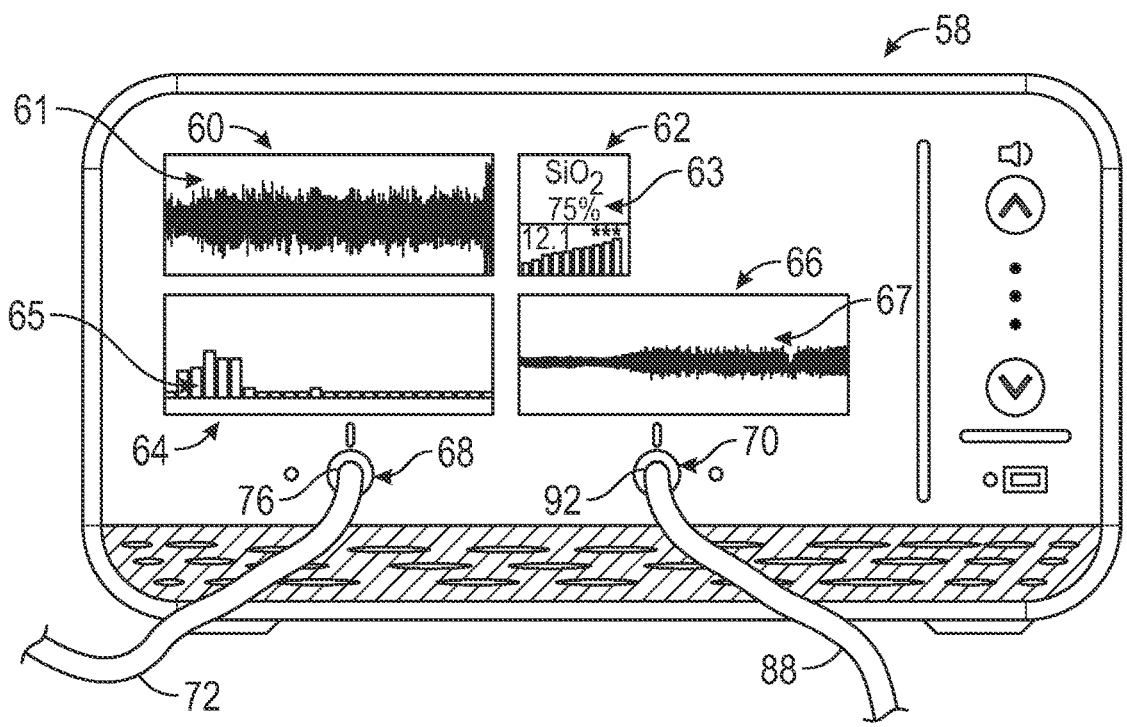
FIG. 5 is another partial elevation view of the blood flow monitor shown in FIG. 3. The second sensor is attached to the monitor using a second extension cable and the monitor is in the on state.

Step 20 can be accomplished by attaching the second sensor to the blood flow monitor to which the first sensor is attached. FIG. 5 illustrates the second sensor 78 attached to the blood flow monitor 58 using a second extension cable 88 that has a first end 90 attached to the second sensor 78 and a second end 92 attached to the blood flow monitor 58 (e.g., second channel port 70). However, in alternative embodiments, a second sensor can be attached directly to a blood flow monitor without using an extension cable.

Step 22 can be accomplished by moving the blood flow monitor from an off state to an on state to observe the blood flow through the first blood vessel and the characteristic of the tissue flap. FIG. 5 illustrates the blood flow monitor 58 in the on state. The first visual display field 60 shows data (e.g., sound data from Doppler probe 46 in graphical form) received from the first sensor 40 relating to blood flow over time 61 (e.g., time domain, amplitude over time, average amplitude over time) for the first blood vessel 42, the second visual display field 62 shows data received from the second sensor 78 relating to the characteristic of the tissue flap (e.g., tissue oxygen saturation levels), the third visual display field 64 shows data relating to the frequency domain of the blood flow over time 65, which can be obtained using Fast Fourier Transforms, and the fourth visual display field 66 shows data relating to a combination of the blood flow over time and the frequency domain of the blood flow over time 67.

Each of the first, third, and fourth visual display fields 60, 64, 66 show a graphic, or a visual representation of data in graphical nature. The first visual display field 60 shows a graphic of the blood flow over time 61 (e.g., sound graphic, visual representation of blood flow velocity in graphical nature) and the data associated with that sound graphic is utilized to create each of the frequency domain of the blood flow over time 65 in the third visual display field 64 and the combination of the blood flow over time and the frequency domain of the blood flow over time 67 in the fourth visual display field 66. The data provided in a visual display field can be shown in real-time, be held or frozen, or a user can select a window of time (e.g., adjustable, user defined) within which the user would like to review data.

Inclusion of the visual display fields 60, 62, 64, 66 are considered advantageous at least because they allow a user to review, or monitor, trend data regarding blood flow over time and tissue health information. For example, the first, third, and fourth visual display fields 60, 64, 66 allow a user to review, or monitor, trend data regarding blood flow over time and the second visual display field 62 allows the user to review, or monitor, data relating to tissue health information. While the blood flow through the first blood vessel over a period of time and the characteristic of the tissue flap have been described as being monitored, alternative embodiments can also include monitoring the characteristic of the tissue flap over a period of time that is the same as, or different from, the period of time which the blood flow through the blood vessel of the tissue flap has been monitored. For example, while the second visual display field 62 has been illustrated as showing a static value relating to tissue health information (e.g., tissue oxygen saturation level), a second visual display field can alternatively provide a characteristic being measured by a second sensor over a period of time (e.g., the same period of time shown within the first display field, a different period of time relative to the period of time shown within the first visual display field). In addition, a blood flow monitor can include functionality for holding maximum values and/or spectrum data over a user-defined window of time and/or for storing data and associated sounds before a signal loss.

Figure 6:
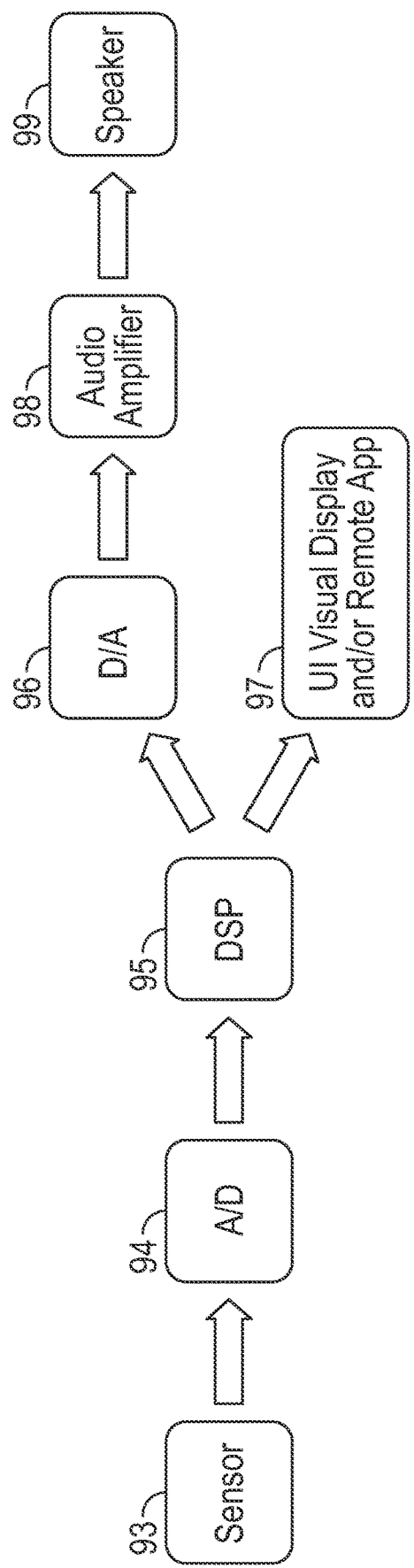
FIG. 6 is an example flowchart illustrating the translation of data obtained from a sensor by a blood flow monitor.

Step 24 can be accomplished using the blood flow monitor and by maintaining the blood flow monitor in the on state such that data received from the first sensor relating to the blood flow through the first blood vessel and the second sensor relating to the characteristic of the tissue flap can be recorded, translated, and/or provided via one or more of the visual display fields 60, 62, 64, 66. FIG. 6 illustrates an example method of translating data from a sensor such that it can be displayed using a visual display field on a blood flow monitor. As shown in FIG. 6, data from a sensor 93 is provided to an analog to digital converter (A/D) 94, which then provides the data to a digital signal processor (DSP) 95. The DSP 95 then provides the data to a digital to analog processor (D/A) 96 and a user interface visual display field and/or a remote app 97. The D/A 96 provides the data to an audio amplifier 98, which then transmits the data to a speaker 99. Each of the A/D 94, DSP 95, D/A 96, user interface visual display field 97, audio amplifier 98, and the speaker 99 is provided within a blood flow monitor, such as those described herein. With respect to a remote app, as described herein, a blood flow monitor can include one or more components capable of receiving and/or transmitting data wirelessly, such as receiving data wirelessly from one or more sensors and/or transmitting data wirelessly to a network such that data received by one or more sensors and/or data displayed within a visual display field can be provided to a remote device (e.g., remote storage device) and/or a user via a remote app (e.g., on a mobile device, on a tablet, on a cellular phone).

A blood flow monitor can be maintained in the on state for any suitable period of time to monitor blood flow through a blood vessel of a tissue flap and/or a characteristic of the tissue flap and selection of a suitable period of time can be based on various considerations, such as the location of the implant site of a tissue flap and/or the type of tissue flap that has been implanted. Examples of periods of time considered suitable to maintain a blood flow monitor in an on state to monitor blood flow through a blood vessel of a tissue flap and/or a characteristic of a tissue flap include one or more seconds, one or more minutes, one or more hours, one or more days, one or more weeks, and any other period of time considered suitable for a particular embodiment. For example, a blood flow monitor can be maintained in an on state to monitor blood flow through a blood vessel of a tissue flap and/or a characteristic of a tissue flap for about 24 hours, about 48 hours, about 72 hours, and any other period of time considered suitable for a particular embodiment.

While the first, second, third, and fourth visual display fields 60, 62, 64, 66 have been illustrated as displaying particular data, a visual display field can display any suitable data and selection of suitable data to display on a visual display field can be based on various considerations, including the data desired by a user relating to an implanted tissue flap. Examples of data considered suitable to display on a visual display field included on a blood flow monitor include data relating to blood flow of a blood vessel included in a tissue flap, tissue health, tissue oxygenation saturation levels, temperature, blood pressure, orifice diameter (e.g., artificial, original), any data over a period of time, user-defined data, data obtained by a physician (e.g., data relating to one or more of the color, the temperature, the capillary refill time, any blood loss, edema, and/or appearance of the flap) that can be displayed as data and/or a photograph, combinations of the data described herein, and any other data considered suitable for a particular embodiment. Any data described herein can be stored and utilized throughout a procedure.

Figure 9:
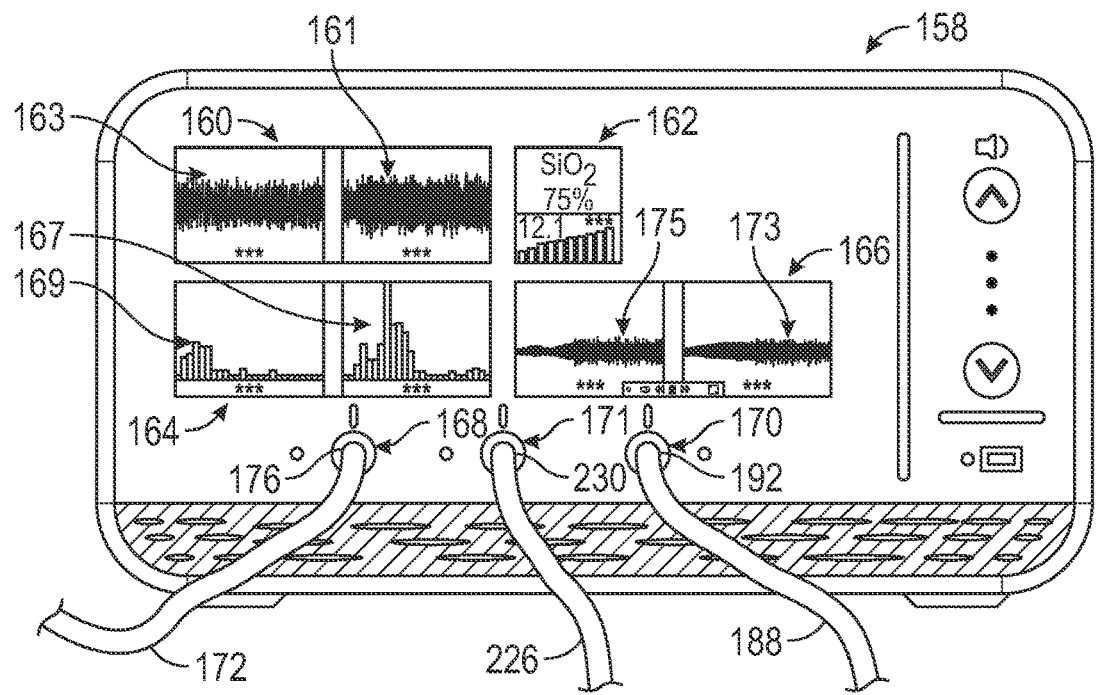
FIG. 9 is a partial elevation view of another example blood flow monitor. The first sensor is attached to the monitor using a first extension cable, the second sensor is attached to the monitor using a second extension cable, the third sensor is attached to the monitor using a third extension cable, and the monitor is in the on state.

While each visual display field 60, 62, 64, 66 has been illustrated as showing a single data set (e.g., blood flow over time, tissue oxygenation saturation level) within a single viewing area within the display field, as described in more detail herein with respect to FIG. 9, a visual display field can alternatively show multiple data sets, each within a separate viewing area. Optionally, a visual display field can include trend lines, such as average amplitude over time, relating to the data displayed within a visual display field. Furthermore, a blood flow monitor can optionally allow a user to record, freeze, and/or store data displayed on a visual display field and/or data obtained by a sensor (e.g., over a period of time (e.g., 15 minutes)) within a local storage device included in the blood flow monitor and/or remotely.

A speaker included in a blood flow monitor can emit any suitable sound, such as Doppler sounds provided by a first sensor to allow a user to listen to sounds relating to historical and/or current blood flow through a blood vessel of a tissue flap. In addition, a blood flow monitor can provided various alerts to provide feedback to a user, such as sound alerts associated with user-defined settings, user-defined trigger points (e.g., change in sound, change in a device event, change in sensor readings), alerts relating to a pre-defined sensor reading, alerts relating to a pre-defined tissue oxygenation saturation level, alerts relating to a pre-defined blood pressure level, alerts relating to a pre-defined orifice diameter, alters relating to the status of the blood flow monitor (e.g., in off state, lost power, malfunctioning), and any other alert considered suitable for a particular embodiment.

Step 26 can be accomplished by reviewing the data provided in the first visual display field, the second visual display field, the third visual display field, and/or the fourth visual display field to determine whether any of the data indicates that the tissue flap requires intervention. For example, if the data displayed in a visual display field (e.g., blood flow over time, characteristic of tissue flap (e.g., tissue oxygenation saturation), frequency domain, combination of frequency domain and time domain) indicates that the data is below a threshold (e.g., user defined), intervention is required. Alternatively, if the data displayed in a visual display field (e.g., blood flow over time, characteristic of tissue flap (e.g., tissue oxygenation saturation), frequency domain, combination of frequency domain and time domain) indicates that the data is above the threshold, intervention is not required.

If intervention is required, step 28 can be accomplished by performing any suitable treatment to accomplish the intervention and such treatment can be based on the data provided in the first visual display field, the second visual display field, the third visual display field, the fourth visual display field, or any combination of the data provided in the first visual display field, the second visual display field, the third visual display field, and the fourth visual display field. Examples of treatments considered suitable to accomplish intervention include repositioning a sensor (e.g., first sensor, second sensor), replacing an implanted tissue flap with a second tissue flap, repositioning the patient, correcting a kink, twist, or tension on a vessel, correcting the design of the anastomosis, treating infection, clot extraction, administering one or more drugs (e.g., anticoagulants, blood thinners), increasing blood pressure, combinations of the treatments described herein, and any other treatment considered suitable for a particular embodiment. If intervention is not required, step 30 can be accomplished by removing the first sensor from the first blood vessel of the tissue flap and removing the second sensor from the tissue flap. Removal of the first sensor can be accomplished by removing any sutures and/or tape from the wire member outside of the body of the patient and applying an axial force on the wire member near the crystal and away from the patient to disengage the crystal from the cuff. The cuff can optionally be left in place around the blood vessel and any opening can be closed (e.g., using sutures). Alternatively, the cuff can be removed from the blood vessel. Removal of the second sensor can be accomplished by applying an axial force on the surface sensor and away from the patient to disengage the surface sensor from the tissue flap.

In alternative embodiments, and depending on the type of sensor being used to provide data to a blood flow monitor, step 26, step 28, and/or step 30 can be omitted from method 10. Step 30 can be omitted, for example, in instances in which the first and second sensors are biodegradable and/or provide data to a blood flow monitor wirelessly. An optional step comprises deactivating the blood flow monitor, which can be accomplished by moving the blood flow monitor from the on state to the off state.

Figure 7:
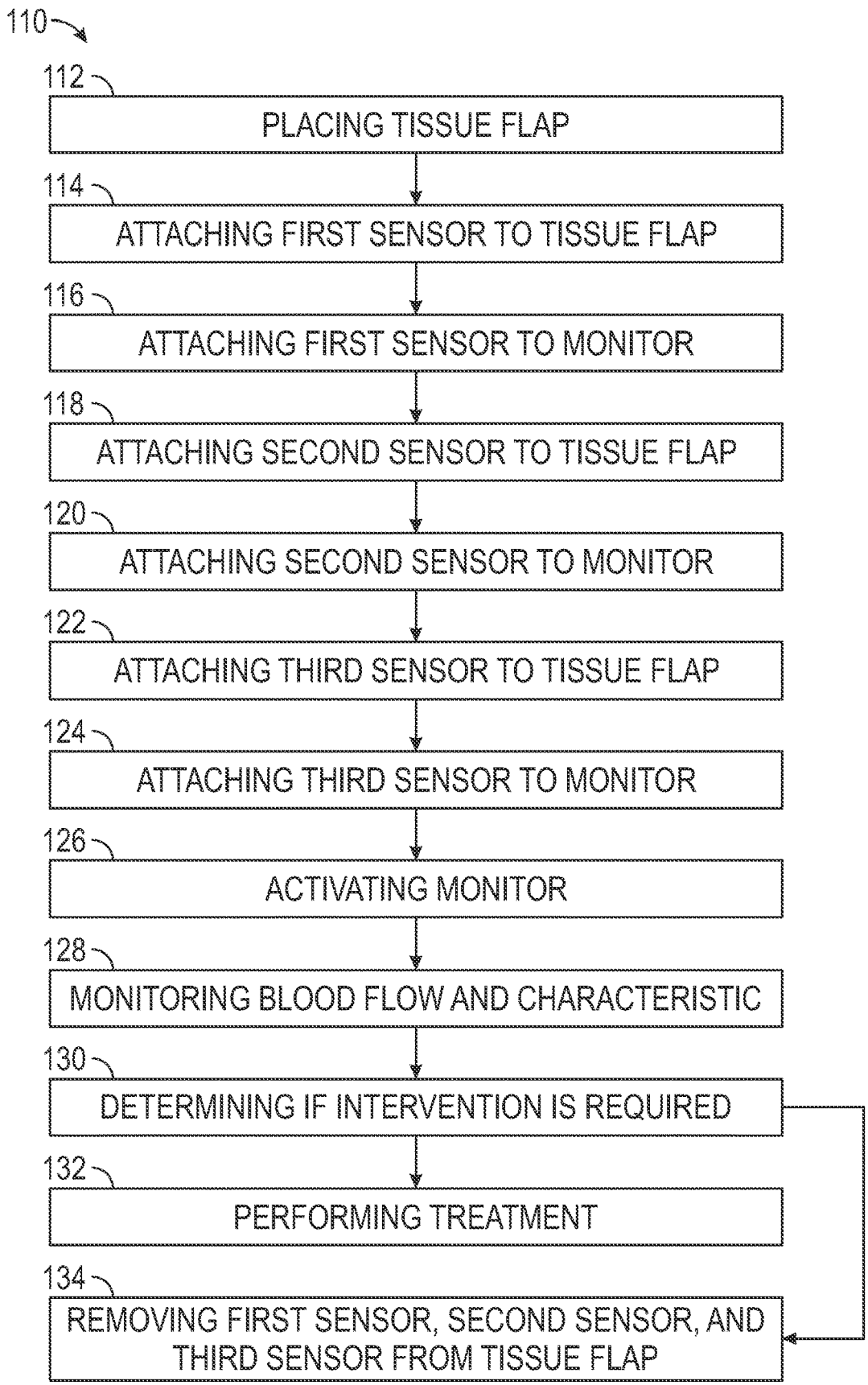
FIG. 7 is a schematic illustration of another example method of monitoring characteristics of tissue.

FIG. 7 is a schematic illustration of another example method 110 of monitoring characteristics of tissue.

A step 112 comprises placing a tissue flap at a point of treatment. The tissue flap includes a section of tissue that includes a first blood vessel and a second blood vessel. Another step 114 comprises attaching a first sensor to the tissue flap to monitor blood flow through the first blood vessel. The first sensor is attached to the tissue flap such that it contacts the first blood vessel. Another step 116 comprises attaching the first sensor to a blood flow monitor that has a first visual display field, a second visual display field, a third visual display field, and a fourth visual display field. Another step 118 comprises attaching a second sensor to the tissue flap to monitor a characteristic of the tissue flap. The second sensor is different than the first sensor. Another step 120 comprises attaching the second sensor to the blood flow monitor. Another step 122 comprises attaching a third sensor to the tissue flap to monitor blood flow through the second blood vessel. The third sensor is attached to the tissue flap such that it contacts the second blood vessel. Another step 124 comprises attaching the third sensor to the blood flow monitor. Another step 126 comprises activating the blood flow monitor to observe the blood flow through the first blood vessel, the characteristic of the tissue flap, and the blood flow through the second blood vessel. Another step 128 comprises monitoring the blood flow through the first blood vessel over a period of time, the characteristic of the tissue flap, and the blood flow through the second vessel over a period of time. Another step 130 comprises determining if the blood flow through the first blood vessel, the characteristic of the tissue flap, and the blood flow through the second blood vessel indicate intervention is required. If intervention is required, another step 132 comprises performing treatment. If intervention is not required, another step 134 comprises removing the first sensor from the tissue flap, removing the second sensor from the tissue flap, and removing the third sensor from the tissue flap.

Step 112 can be accomplished as described herein with respect to step 12 and using a tissue flap that includes a first blood vessel and a second blood vessel.

Figure 8:
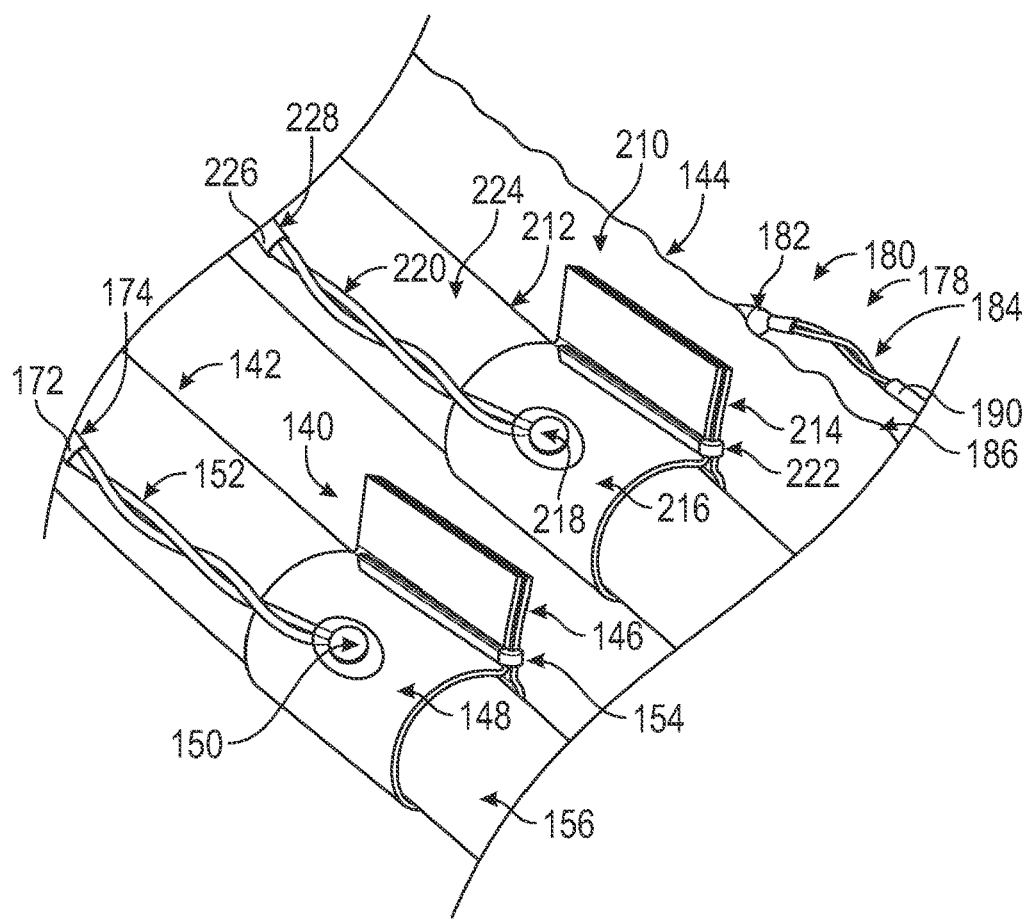
FIG. 8 is a partial perspective view of a first sensor, a second sensor, and a third sensor attached to a tissue flap.

Step 114 can be accomplished as described herein with respect to step 14. FIG. 8 illustrates a first sensor 140 contacting a first blood vessel 142 of a tissue flap 144. In the illustrated embodiment, the first sensor 140 is a Doppler probe 146 that includes a cuff 148, a probe crystal 150 attached to the cuff 148, and a wire member 152 attached to the probe crystal 150. The first sensor 140 is attached to the first blood vessel 142 by wrapping the cuff 148 around the first blood vessel 142 and attaching the cuff 148 directly to the first blood vessel 142 (e.g., surgically) using a surgical clip 154. The first sensor 140 allows for monitoring of blood flow within the first blood vessel 142 intraoperatively and postoperatively following completion of a procedure (e.g., reconstructive procedure). In the illustrated embodiment, the first sensor 140 is disposed deep within the tissue flap 144 (i.e., beneath a surface of the flap 144, subcutaneously) and is attached to a vein 156.

Step 116 can be accomplished by attaching the first sensor to any suitable blood flow monitor that has a first visual display field, a second visual display field, a third visual display field, and a fourth visual display field. FIG. 9 illustrates an example blood flow monitor 158 considered suitable to attach the first sensor 140. The blood flow monitor 158 has a first visual display field 160, a second visual display field 162, a third visual display field 164, a fourth visual display field 166, a first channel port 168, a second channel port 170, and a third channel port 171. The blood flow monitor 158 is moveable between an off state and an on state. FIG. 9 illustrates the blood flow monitor 158 in the on state. In the illustrated embodiment, the first sensor 140 is attached to the blood flow monitor 158 using a first extension cable 172 that has a first end 174 attached to the first sensor 140 and a second end 176 attached to the blood flow monitor 158 (e.g., first channel port 168). However, in alternative embodiments, a first sensor can be attached directly to a blood flow monitor without using an extension cable.

Step 118 can be accomplished as described herein with respect to step 18. FIG. 8 illustrates a second sensor 178 contacting the tissue flap 144. The second sensor 178 is different than the first sensor 140. In the illustrated embodiment, the second sensor 178 is a StO2 sensor 180 that includes a surface sensor 182 and a wire member 184 attached to the surface sensor 182. The second sensor 178 is attached to a surface 186 of the tissue flap 144 (e.g., superficially relative to the first sensor 140) by attaching the surface sensor 182 directly to the surface 186 of the tissue flap 144 (e.g., using adhesive). The second sensor 178 allows for monitoring of a characteristic of the tissue flap 144 that is different than the characteristic being monitored by the first sensor 140. In the illustrated embodiment, the second sensor 178 allows for monitoring of the tissue oxygenation saturation of the tissue flap 144 intraoperatively and postoperatively following completion of a procedure (e.g., reconstructive procedure).

Step 120 can be accomplished by attaching the second sensor to the blood flow monitor to which the first sensor is attached. FIG. 9 illustrates the second sensor 178 attached to the blood flow monitor 158 using a second extension cable 188 that has a first end 190 attached to the second sensor 178 and a second end 192 attached to the blood flow monitor 158 (e.g., second channel port 170). However, in alternative embodiments, a second sensor can be attached directly to a blood flow monitor without using an extension cable.

Step 122 can be accomplished as described herein with respect to step 14 and by attaching any suitable third sensor to the tissue flap such that the third sensor contacts a blood vessel (e.g., a first blood vessel, a second blood vessel). FIG. 8 illustrates a third sensor 210 contacting a second blood vessel 212 of the tissue flap 144. In the illustrated embodiment, the second sensor 210 is a Doppler probe 214 that includes a cuff 216, a probe crystal 218 attached to the cuff 216, and a wire member 220 attached to the probe crystal 218. The third sensor 210 is attached to the second blood vessel 212 by wrapping the cuff 216 around the second blood vessel 212 and attaching the cuff 216 directly to the second blood vessel 212 (e.g., surgically) using a surgical clip 222. The third sensor 210 allows for monitoring of blood flow within the second blood vessel 212 intraoperatively and postoperatively following completion of a procedure (e.g., reconstructive procedure). In the illustrated embodiment, the third sensor 210 is disposed deep within the tissue flap 144 (i.e., beneath a surface of the flap 144, subcutaneously) and is attached to an artery 224.

Step 124 can be accomplished by attaching the third sensor to the blood flow monitor to which the first sensor and the second sensor are attached. FIG. 9 illustrates the third sensor 210 attached to the blood flow monitor 158 using a third extension cable 226 that has a first end 228 attached to the third sensor 210 and a second end 230 attached to the blood flow monitor 158 (e.g., third channel port 171). However, in alternative embodiments, a third sensor can be attached directly to a blood flow monitor without using an extension cable.

Step 126 can be accomplished as described herein with respect to step 22 and to observe the blood flow through the first blood vessel, the characteristic of the tissue flap, and the blood flow through the second blood vessel. FIG. 9 illustrates the blood flow monitor 158 in the on state. The first visual display field 160 shows data (e.g., sound data from Doppler probe 146 in graphical form) received from the first sensor 140 relating to blood flow over time 161 (e.g., time domain, amplitude over time) for the first blood vessel 142 and data (e.g., sound data from Doppler probe 214 in graphical form) received from the second sensor 210 relating to blood flow over time 163 (e.g., time domain, amplitude over time) for the second blood vessel 212. The second visual display field 162 shows data received from the second sensor 178 relating to the characteristic of the tissue flap being monitored by the second sensor 178 (e.g., tissue oxygen saturation levels). The third visual display field 164 shows data relating to the frequency domain of the blood flow over time 167 for the first blood vessel 142 and data relating to the frequency domain of the blood flow over time 169 for the second blood vessel 212. The fourth visual display field 166 shows data relating to a combination of the blood flow over time and the frequency domain of the blood flow over time 173 for the first blood vessel 142 and a combination of the blood flow over time and the frequency domain of the blood flow over time 175 for the second blood vessel 212. While the first, third, and fourth visual display fields 160, 164, 166 have been illustrated as including data relating to both the first blood vessel 142 and the second blood vessel 212, the data shown could alternatively be provided in separate visual display fields provided on a blood flow monitor. The inclusion of data relating to both the first blood vessel 142 and the second blood vessel 212 provides a mechanism for comparing data in real-time, and/or trend data, to determine if intervention is required, as described herein. For example, a correlated change in blood flow on both graphics could indicate that intervention, or further investigation, is required.

Inclusion of the visual display fields 160, 162, 164, 166 are considered advantageous at least because they allow a user to review, or monitor, trend data regarding blood flow over time for first and second blood vessels and tissue health information. For example, the first, third, and fourth visual display fields 160, 164, 166 allow a user to review, or monitor, trend data regarding blood flow over time for first and second blood vessels 142, 212 and the second visual display field 162 allows for the user to review, or monitor, data relating to tissue health information.

Step 128 can be accomplished as described herein with respect to step 24. For example, step 128 can be accomplished by maintaining the blood flow monitor in the on state such that data received from the first sensor relating to the blood flow through the first blood vessel, the second sensor relating to the characteristic of the tissue flap, and the third sensor relating to blood flow through the second blood vessel can be recorded, translated, and provided via one or more of the visual display fields 160, 162, 164, 166.

Step 130 can be accomplished as described herein with respect to step 26. Step 132 can be accomplished as described herein with respect to step 28.

Step 134 can be accomplished by removing the first sensor from the first blood vessel of the tissue flap, removing the second sensor from the tissue flap, and removing the third sensor from the second blood vessel of the tissue flap. Removal of the first sensor and the second sensor can be accomplished as described herein with respect to step 30. Removal of the third sensor can be accomplished by removing any sutures and/or tape from the wire member outside of the body of the patient and applying an axial force on the wire member near the crystal and away from the patient to disengage the crystal from the cuff. The cuff can optionally be left in place around the blood vessel and any opening can be closed (e.g., using sutures). Alternatively, the cuff can be removed from the blood vessel.

In alternative embodiments, and depending on the type of sensor being used to provide data to a blood flow monitor, step 130, step 132, and/or step 134 can be omitted from method 110. Step 134 can be omitted, for example, in instances in which the first, second, and third sensors are biodegradable and/or provide data to a blood flow monitor wirelessly. An optional step comprises deactivating the blood flow monitor, which can be accomplished by moving the blood flow monitor from the on state to the off state.

Figure 10:
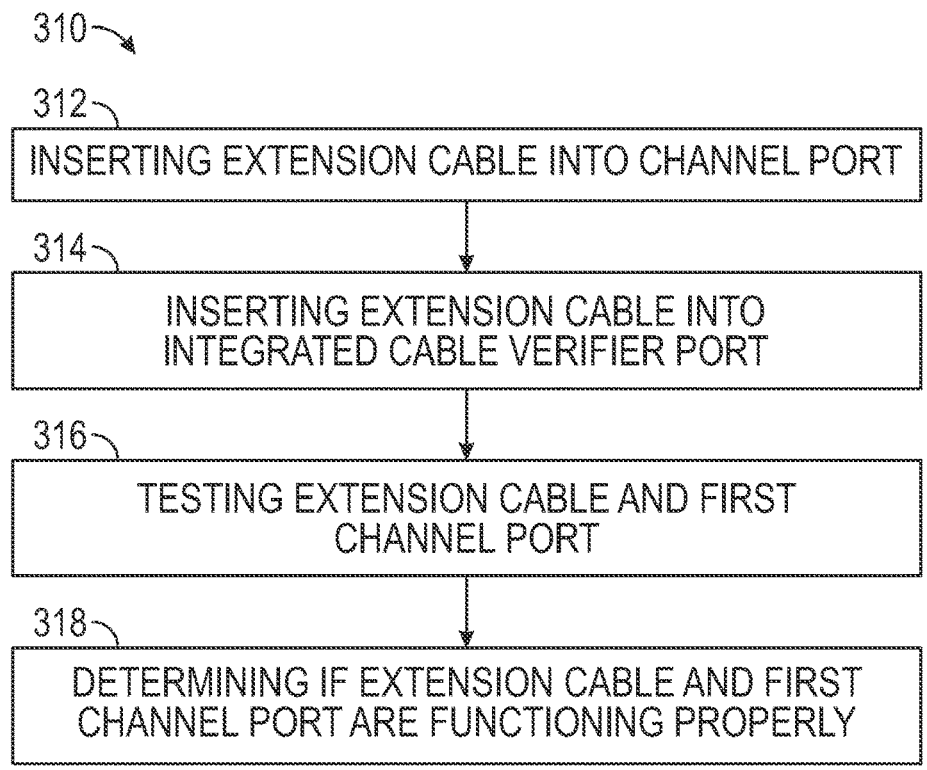
FIG. 10 is a schematic illustration of an example method of verifying the functionality of an extension cable and a channel port of a blood flow monitor.

FIG. 10 is a schematic illustration of an example method 310 of verifying the functionality of an extension cable and a channel port of a blood flow monitor.

A step 312 comprises inserting a first end of an extension cable into a first channel port of a monitor. The monitor includes the first channel port and an integrated cable verifier port. Another step 314 comprises inserting a second end of the extension cable into the integrated cable verifier port. Another step 316 comprises testing the extension cable and the first channel port. Another step 318 comprises determining if the extension cable and the first channel port are functioning properly.

Step 312 can be accomplished using any suitable extension cable and selection of a suitable extension cable can be based on various considerations, such as the type of sensor and/or blood flow monitor to which it is intended to attach the extension cable. Examples of extension cables considered suitable to complete a method described herein include Doppler extension cables, Swartz Doppler extension cables, blood flow monitor extension cables, extension cables compatible with tissue oxygen saturation sensors, temperature sensors, blood pressure sensors, and/or orifice diameter sensors (e.g., artificial, original), and any other extension cable considered suitable for a particular embodiment.

Figure 11:
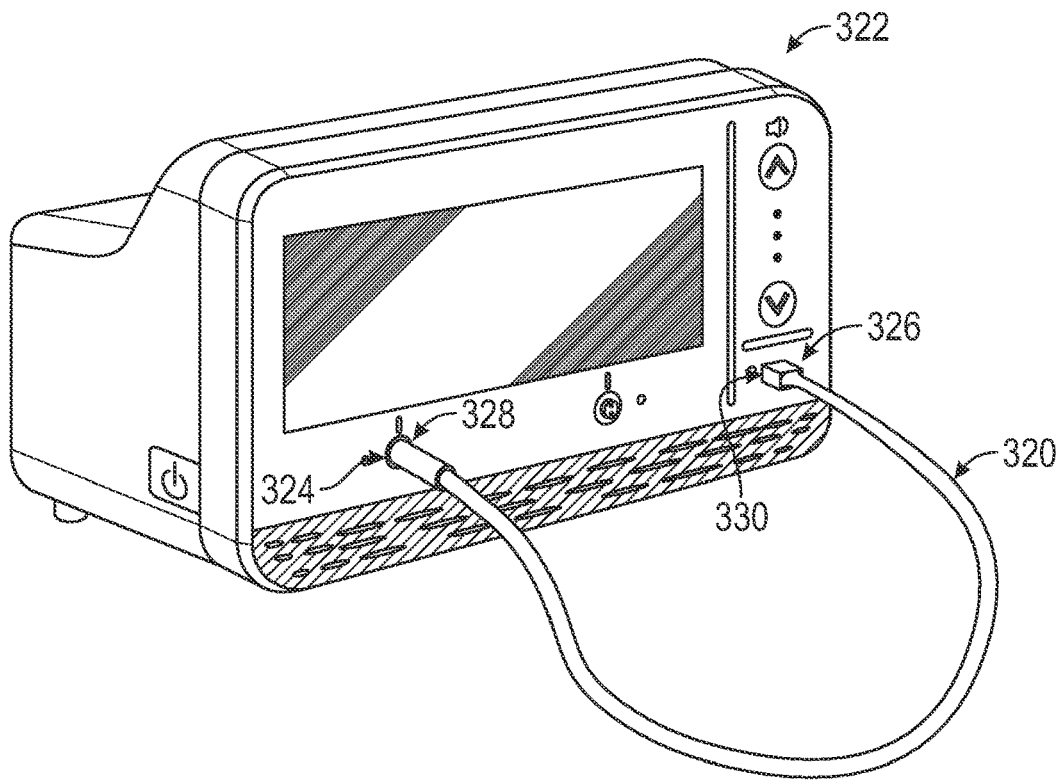
FIG. 11 is a perspective view of another example blood flow monitor that includes an integrated cable verifier port. The extension cable has been inserted into the channel port and the integrated cable verifier port.

Step 312 can be accomplished by applying an axial force on an extension cable directed toward a blood flow monitor until the first end of the extension cable is disposed within the first channel port. Step 314 can be accomplished by applying an axial force on the extension cable directed toward the blood flow monitor until the second end of the extension cable is disposed within the integrated cable verifier port. FIG. 11 illustrates an extension cable 320 and an example blood flow monitor 322 that can be used to complete method 310. The extension cable 320 has a first end 324 and a second end 326. The monitor 322 has a first channel port 328 and an integrated cable verifier port 330. The first end 324 of the extension cable 320 is attached to the first channel port 328 of the blood flow monitor 322 and the second end 326 of the extension cable 320 is attached to the integrated cable verifier port 330 of the blood flow monitor 322.

Step 316 can be accomplished by the blood flow monitor, through the integrated cable verifier port, stimulating the extension cable and the first channel port to test the extension cable and the first channel port. An LED indicator and/or user interface (UI) pop up provided on the blood flow monitor can provide the results of the test indicating whether the extension cable and the first channel port are functioning properly. Optionally, a monitor can automatically recognize when an extension cable has been inserted into an integrated cable verifier port and automatically test the extension cable and associated port upon inserting the extension cable into the integrated cable verifier port.

Step 318 can be accomplished by reviewing the data provided by the LED indicator and/or UI pop up. If the data reflects that the extension cable and channel port are functioning properly, they both can be used as described herein to complete a method of monitoring characteristics of tissue. If the data reflects that the extension cable and channel port are not functioning properly, additional steps comprise: removing the extension cable from the first channel port; removing the extension cable from the integrated cable verifier port; inserting a second extension cable into the first channel port; inserting the second extension cable into the integrated cable verifier port; testing the second cable and the first channel port; and determining if the second cable and the first channel port are functioning properly. Each of these additional steps can be accomplished as described herein. If the data reflects that the second extension cable and channel port are functioning properly, they both can be used as described herein to complete a method of monitoring characteristics of tissue. This outcome indicates that the original extension cable is faulty. If the data reflects that the extension cable and channel port are not functioning properly, the channel port may be faulty.

Method 310 provides a mechanism for real-time bedside testing of a channel port of a blood flow monitor and an extension cable being used to complete a method of monitoring characteristics of tissue, as described herein. Conventionally, channel/cable verifiers are separate members secured to a monitor using a snap clip when they are not in use. As a result, when the monitor is relocated, the channel/cable verifier can become dislodged from the clip and lost, which prevents users from testing channel ports and extension cables. The monitor 322 is considered advantageous at least because it integrates the cable verifier and prevents loss of the verifier during transit and use of the monitor.

Method 310 can optionally be incorporated into a method of monitoring characteristics of tissue, such as those described herein. For example, the steps described with respect to method 310 can be incorporated into method 10 and can be completed prior to, subsequent to, or concurrently with step 14, step 16, step 18, and/or step 20 to confirm the proper functioning of any extension cables 72, 88 being used to attach the first sensor 40 and/or the second senor 78 to the blood flow monitor 58. In addition, the steps described with respect to method 310 can be incorporated into method 110 and can be completed prior to, subsequent to, or concurrently with step 114, step 116, step 118, step 120, step 122, and/or step 124 to confirm the proper functioning of any extension cables 172, 188, 226 being used to attach the first sensor 140, the second senor 178, and/or third sensor 210 to the blood flow monitor 158. Furthermore, a monitor that includes an integrated cable verifier port, such as monitor 322, can be used to complete one or more of the methods described herein, such as method 10 and/or method 110.

The methods of monitoring characteristics of tissue described herein are considered advantageous at least because they provide graphic visualizations (e.g., graphical trend) of the data being provided on a visual display field. For example, a user visualizing a velocity response of the blood flow over time can determine whether there is a positive or stable trend, which could indicate there is adequate blood flow, or if there is a negative or abrupt trend, which could indicate that further inspection of the treatment area is needed. Furthermore, a temporary negative trend could indicate that the blood pressure of the patient is going down or the vessel is dilating due to the swelling going down at the site. Alternatively, a trend could also indicate whether a brief interruption in the signal may be attributed to a collapsed vessel due to patient movement or a sensor becoming dislodged from the tissue. Time zero could be understood by reviewing the data on the visual display field and identifying when loss of blood flow occurred. This allows a user to troubleshoot an event that may be happening erratically, such as patient movement, or identify when intervene may be required before tissue loss (e.g., flap loss). By monitoring the data, graphics, and/or trend data provided on a blood flow monitor during, or subsequent to a procedure, unnecessary intervention associated with false positives and tissue flap loss associated with false negatives can be prevented.

In addition to the above, the methods of monitoring characteristics of tissue described herein are considered advantageous at least because they not only provide a mechanism for monitoring blood flow, but also provide a mechanism for monitoring a characteristic of tissue (e.g., tissue oxygen saturation). Such dual monitoring provides multiple sets of data to a user (e.g., physician) such that interventions on tissue flaps can be completed more efficiently and only when intervention is required. For example, in embodiments in which the characteristic of tissue being monitored relates to tissue oxygen saturation, the data associated with tissue oxygen saturation enable the detection of compromises in tissue viability prior to the appearance of overt clinical signs of such compromises while the additional data associated with blood flow provide conclusive evidence of tissue viability. Therefore, as described herein, by monitoring both blood flow data and a characteristic of tissue, unnecessary intervention associated with false positives and tissue flap loss associated with false negatives can be prevented.

Those with ordinary skill in the art will appreciate that various modifications and alternatives for the described and illustrated embodiments can be developed in light of the overall teachings of the disclosure, and that the various elements and features of one example described and illustrated herein can be combined with various elements and features of another example without departing from the scope of the invention. Accordingly, the particular arrangement of elements and steps disclosed herein have been selected by the inventor(s) simply to describe and illustrate examples of the invention and are not intended to limit the scope of the invention or its protection, which is to be given the full breadth of the appended claims and any and all equivalents thereof.

What is claimed is:

1. A method of monitoring characteristics of tissue comprising:
    placing a tissue flap at a point of treatment, the tissue flap comprising a section of tissue that includes a first blood vessel;
    attaching a first sensor to the tissue flap to monitor blood flow through the first blood vessel, the first sensor contacting the first blood vessel;
    attaching the first sensor to a blood flow monitor having a first visual display field and a second visual display field;
    attaching a second sensor to the tissue flap to monitor a characteristic of the tissue flap, the second sensor being different than the first sensor;
    attaching the second sensor to the blood flow monitor;
    activating the blood flow monitor to observe the blood flow through the first blood vessel and the characteristic of the tissue flap, the first visual display field showing blood flow over time, the second visual display field showing the characteristic of the tissue flap; and
    monitoring the blood flow through the first blood vessel over a period of time and the characteristic of the tissue flap using the blood flow monitor.

2. The method of claim 1, further comprising determining if the blood flow through the first blood vessel and the characteristic of the tissue flap indicate intervention is required, if intervention is required the method further comprises performing treatment to accomplish the intervention, if intervention is not required the method further comprises removing the first sensor from the tissue flap and removing the second sensor from the tissue flap.

3. The method of claim 1, wherein the first sensor is a Doppler probe.

4. The method of claim 1, wherein the first sensor is attached to the tissue flap subcutaneously.

5. The method of claim 1, wherein the second sensor is a StO2 sensor.

6. The method of claim 1, wherein the second sensor is attached to the tissue flap superficially relative to the first sensor.

7. The method of claim 1, wherein attaching the second sensor to the tissue flap to monitor the characteristic of the tissue flap comprises attaching the second sensor to a surface of the tissue flap to monitor the characteristic of the tissue flap.

8. The method of claim 1, wherein the second visual display field shows the characteristic of the tissue flap over time.

9. The method of claim 8, wherein the second sensor is a StO2 sensor.

10. The method of claim 1, wherein the blood flow monitor has a third visual display field showing a frequency domain of the blood flow over time.

11. The method of claim 10, wherein the blood flow monitor has a fourth visual display field showing a combination of the blood flow over time and the frequency domain of the blood flow over time.

12. The method of claim 1, wherein the first blood vessel is a vein.

13. The method of claim 1, wherein the first blood vessel is an artery.

14. The method of claim 1, wherein the section of tissue includes a second blood vessel;
    further comprising attaching a third sensor to the second blood vessel to monitor blood flow through the second blood vessel, the third sensor contacting the second blood vessel; and
    further comprising attaching the third sensor to the blood flow monitor.

15. The method of claim 14, wherein the first blood vessel is a vein; and
    wherein the second blood vessel is an artery.

16. The method of claim 14, wherein the first visual display field shows blood flow over time for the first blood vessel and blood flow over time for the second blood vessel.

17. The method of claim 16, wherein the blood flow monitor has a third visual display field showing a frequency domain of the blood flow over time for the first blood vessel and a frequency domain of the blood flow over time for the second blood vessel.

18. The method of claim 17, wherein the blood flow monitor has a fourth visual display field showing a combination of the blood flow over time and the frequency domain of the blood flow over time for the first blood vessel and a combination of the blood flow over time and the frequency domain of the blood flow over time for the second blood vessel.

19. A method of monitoring characteristics of tissue comprising:
    placing a tissue flap at a point of treatment, the tissue flap comprising a section of tissue that includes a first blood vessel;
    attaching a first sensor to the tissue flap to monitor blood flow through the first blood vessel, the first sensor contacting the first blood vessel, the first sensor being a Doppler probe;

attaching the first sensor to a blood flow monitor having a first visual display field and a second visual display field;

attaching a second sensor to the tissue flap to monitor a characteristic of the tissue flap, the second sensor being a StO2 sensor;

attaching the second sensor to the blood flow monitor;

activating the blood flow monitor to observe the blood flow through the first blood vessel and the characteristic of the tissue flap, the first visual display field showing blood flow over time, the second visual display field showing the characteristic of the tissue flap;

monitoring the blood flow through the first blood vessel over a period of time and the characteristic of the tissue flap using the blood flow monitor; and determining if the blood flow through the first blood vessel and the characteristic of the tissue flap indicate intervention is required, if intervention is required the method further comprises performing treatment to accomplish the intervention, if intervention is not required the method further comprises removing the first sensor from the tissue flap and removing the second sensor from the tissue flap.

20. A method of monitoring characteristics of tissue comprising:

placing a tissue flap at a point of treatment, the tissue flap comprising a section of tissue that includes a first blood vessel;

attaching a first sensor to the tissue flap to monitor blood flow through the first blood vessel, the first sensor contacting the first blood vessel and attached to the tissue flap subcutaneously, the first sensor being a Doppler probe;

attaching the first sensor to a blood flow monitor having a first visual display field, a second visual display field, a third visual display field, and a fourth visual display field;

attaching a second sensor to the tissue flap to monitor a characteristic of the tissue flap, the second sensor being an StO2 sensor and attached to the tissue flap superficially relative to the first sensor;

attaching the second sensor to the blood flow monitor;

activating the blood flow monitor to observe the blood flow through the first blood vessel and the characteristic of the tissue flap, the first visual display field showing blood flow over time, the second visual display field showing the characteristic of the tissue flap, the third visual display field showing a frequency domain of the blood flow over time, the fourth visual display field showing a combination of the blood flow over time and the frequency domain of the blood flow over time;

monitoring the blood flow through the first blood vessel over a period of time and the characteristic of the tissue flap using the blood flow monitor; and determining if the blood flow through the first blood vessel and the characteristic of the tissue flap indicate intervention is required, if intervention is required the method further comprises performing treatment to accomplish the intervention, if intervention is not required the method further comprises removing the first sensor from the tissue flap and removing the second sensor from the tissue flap.

* * * * *